United States Patent
Blanks et al.

(10) Patent No.: US 10,792,260 B2
(45) Date of Patent: Oct. 6, 2020

(54) RETINOPATHY TREATMENT

(71) Applicant: CHS Pharma, Inc., Miami, FL (US)

(72) Inventors: Janet C. Blanks, Boca Raton, FL (US); Howard Malcolm Prentice, Boca Raton, FL (US); Herbert Weissbach, Boynton Beach, FL (US)

(73) Assignee: CHS PHARMA, INC., Miami, FL (US)

( * ) Notice: Subject to any disclaimer, the term of this patent is extended or adjusted under 35 U.S.C. 154(b) by 562 days.

(21) Appl. No.: 14/861,009

(22) Filed: Sep. 22, 2015

(65) Prior Publication Data

US 2016/0074350 A1    Mar. 17, 2016

Related U.S. Application Data

(63) Continuation of application No. PCT/US2014/031712, filed on Mar. 25, 2014.

(60) Provisional application No. 61/804,851, filed on Mar. 25, 2013.

(51) Int. Cl.
| | | |
|---|---|---|
| *A61K 31/192* | (2006.01) | |
| *A61K 9/00* | (2006.01) | |
| *A61K 9/08* | (2006.01) | |

(52) U.S. Cl.
CPC .......... *A61K 31/192* (2013.01); *A61K 9/0048* (2013.01); *A61K 9/08* (2013.01)

(58) Field of Classification Search
CPC ........... A61K 31/192; A61K 9/00; A61K 9/08
See application file for complete search history.

(56) References Cited

U.S. PATENT DOCUMENTS

| | | |
|---|---|---|
| 5,053,429 A | 10/1991 | Hirsch |
| 5,401,774 A | 3/1995 | Pamukcu |
| 5,608,067 A | 3/1997 | Afonso |
| 6,201,028 B1 | 3/2001 | Shiff |
| 7,129,374 B2 | 10/2006 | Weissbach |
| 7,414,139 B2 | 8/2008 | Weissbach |
| 8,258,181 B2 | 9/2012 | Weissbach |
| 8,487,128 B2 | 7/2013 | Weissbach |
| 8,871,971 B2 | 10/2014 | Weissbach |
| 2003/0191098 A1 | 10/2003 | D'Amato |
| 2005/0119262 A1 | 6/2005 | Wax |
| 2007/0116730 A1* | 5/2007 | Simmons ............. A61K 9/0017 424/400 |
| 2008/0119559 A1 | 5/2008 | Weissbach |
| 2009/0326073 A1 | 12/2009 | Weissbach |
| 2010/0069331 A1 | 3/2010 | Weissbach |
| 2010/0260864 A1 | 10/2010 | Weissbach |
| 2012/0295979 A1 | 11/2012 | Prentice |

FOREIGN PATENT DOCUMENTS

| | | |
|---|---|---|
| WO | 03063908 | 8/2003 |
| WO | 2007130575 | 11/2007 |

OTHER PUBLICATIONS

Pediatrics vol. 76 No. 2, Aug. 1985.*
Moench et al.: "Sulindac confers high level ischemic protection to the heart through late preconditioning mechanisms," Proceedings of the National Academy of Sciences, Nov. 17, 2009, vol. 106, No. 46: 19611-19616.
Krishna et al.: "The influence of sulindac on diabetic cardiomyopathy: A non-invasive evaluation by Doppler echocardiography in streptozotocin-induced diabetic rates," Vascular Pharmacology, 2005, vol. 43:91-100.
Prentice, W. et al.: "Methionine sulfoxide reductase-A and sulindac protect cardiac myocytes against programmed death caused by hypoxia/reoxygenation or H202," Biosis Database (Abstract only), Oct. 26, 2004, 2 pages.
Henrich et al.: "Renal hemodynamic effects of therapeutic plasma levels of sulindac sulfide during hemorrhage," Kidney International (Abstract only), 1986, vol. 29, No. 2, 1 page.
O'Connor, R. et al.: "Increased anti-tumour efficacy of doxorubicin when combined with sulindac in a xenograft model of an MRP-1-positive human lung cancer," Anticancer Research, 2004, vol. 24:457-464.
Kim, H. et al: "Combination of arsenic trioxide with sulindac augments cell death and induced apoptosis via activation of caspase cascade in NCI-H157 human lung carcinoma cells," Proc Amer Assoc Cancer Res., 2004, vol. 45., 2 pages.
Athar, M. et al.: "Photoprotective effects of sulindac against ultraviolet B-induced phototoxicity in the skin of SKH-1 hairless mice," Toxicol Appl Pharmacol. (Abstract only), Mar. 15, 2004, vol. 195(3): 370-378.
Sharma, YR. et al.: "Topical sulindac therapy in diabetic senile cataracts: cataract-IV," Indian J Ophthalmol. (Abstract only), 1989, vol. 37(3): 127-133.
Patani, G. and Edmond J. LaVoie: "Bioisosterism: A rational approach in drug design," Chem. Rev., 1996, Vo. 96: 3147-3176.
Spector, D. et al.: New membrance-associated and soluble peptide methionine sulfoxide reductases in *Escherichia coli*, Biochem Biophys Res Commun. (Abstract only), Mar. 7, 2003, vol. 303(2): 284-9.
Fukuyama, et al.: "Stereocontrolled synthesis of (−)-hapalindole G," J.Am.Chem.Soc. (Abstract only), 1994, vol. 116(7): 3125-3126.
Hartley, A. et al.: "Complex I inhibitors induce dose-dependent apoptosis in PC 12 cells: relevance to Parkinson's disease," J Neurochem. (Abstract only), 1994, vol. 63(5): 1987-90.
Moskovitz, J. et al.: "Methionine sulfoxide reductase (MsrA) is a regulator of antioxidant defense and lifespan in mammals," PNAS, Nov. 6, 2001, vol. 98(23): 12920-12925.
Brot, N. et al.: "Reduction of N-acetyl methionine sulfoxide: A simply assay for peptide methionine sulfoxide reductase," Analytical Biochemistry (Abstract only), May 1982, vol. 122 (2): 291-294.
Moskovitz, J. et al.: "Cloning and expression of a mammalian gene involved in the reduction of methionine sulfoxide residues in proteins," Proc. Natl. Acad. Sci. USA, Mar. 1996, vol. 93: 2095-2099.

(Continued)

*Primary Examiner* — Zohreh A Fay
(74) *Attorney, Agent, or Firm* — Stanley A. Kim

(57) ABSTRACT

A method of preventing degeneration of photoreceptor cells in an eye of a mammalian subject includes the step of administering pharmaceutical composition comprising a sulindac agent to the eye of the subject.

11 Claims, 8 Drawing Sheets

(56) References Cited

OTHER PUBLICATIONS

Minetti, G. et al.: Reduction of DABS-L-methionine-dl-sulfoxide by protein methionine sulfoxide reductase from polymorphonuclear leukocytes: stereospecificity towars the 1-sulfoxide, Ital J Biochem. (Abstract only), Nov.-Dec. 1994, vol. 43(6): 273-83.

Grimaud, R. et al.: "Repair of oxidixed proteins," The Journal of Biological Chemistry, Dec. 2001, vol. 276(52):48915-48920.

Rahman, M. et al.: "Highl level expression and purification of peptide methionine sulfoxide reductase in *Escherichia coli*," Cell Mol Biol. (Abstract only), Aug. 1992, vol. 38(5):529-42.

Etienne, F. et al.: "A methionine sulfoxide reductase in *Escherichia coli* that reduces the R enantiomer of methionine sulfoxide," Biochem Biophys Res Commun. (Abstract only), Jan. 2003, vol. 300(2): 378-82.

Kita, Y. et al.: "Enantioselective total synthesis of a potent antitumor antibiotic, fredericamycin A," Journal of the American Chemical Society (Abstract only), 2001, vol. 123(14):3214-3222.

Conte, V. et al.: "Asymmetric oxidation of thioethers: Enantioselectve synthesis of beta-hydroxysulfoxides by direct oxidation," Tetrajedron Letters (Abstract only), 1989, vol. 30 (36):4859-4862.

O'Donnell, M.J. et al.: "The stereoselective synthesis of .alpha.-amino acids by phase-transfer catalysis," Journal of the American Chemical Society (Abstract only), 1989, vol. 111(6):2353-2355.

Rosen, D.R., et al.: "Mutations in cu/Zn superoxide dismutgase gene are associated with familial amyotrophic lateral sclerosis," Nature (Abstract only), 1993, vol. 362:59-62.

Weissbach, H. et al.: "Peptide methionine sulfoxide reductase: structure, mechanism of action, and biological function," Archives of Biochemistry and Biophysics (Abstract only), Jan. 2002, vol. 397(2):172-178.

Ruan, H. et al.: "High-quality life extension by the enzyme peptide methionine sulfoxide reductase," PNAS, Mar. 2002, vol. 99(5):2748-2753.

Ejiri, S. et al.: "The purification of methionine sulfoxide reductase from *Escherichia coil*," Analytical Biochemistry (Abstract only), Mar. 1980, vol. 102(2):1.

\* cited by examiner

RETINOPATHY TREATMENT

CROSS-REFERENCE TO RELATED APPLICATIONS

The present application is a continuation application under 35 U.S.C. § 120 of co-pending International Patent Application Number PCT/US2014/031712, filed on Mar. 25, 2014, which designated the United States and claimed priority of U.S. provisional patent application Ser. No. 61/804,851 filed on Mar. 25, 2013.

FIELD OF THE INVENTION

The invention relates generally to the fields of ophthalmology, pharmaceuticals, and medicine. More particularly, the invention relates to the use of sulindac agents to protect retinal cells against oxidative damage.

BACKGROUND

In mammalian eyes, the most direct pathway for image formation is from photoreceptor cells to bipolar cells to retinal ganglion cells. The light sensitive photoreceptors pass on the information to the bipolar cells via synaptic interactions and the bipolar cells then send the message to the ganglion cells. The ganglion cells fire action potentials which propagate down the optic nerve to the brain for processing. The key role played by photoreceptors in the process of vision implies that any damage to these cells will be highly deleterious for the normal physiology and functioning of the eye. The health of photoreceptor cells is linked to the function of the adjacent retinal pigment epithelium (RPE) that is a monolayer between the retina and the choroid.

The visual impairment in advanced age-related macular degeneration (AMD) is associated with photoreceptor loss in the macula, the central area of the retina responsible for acuity and color vision. Photoreceptor degeneration is usually preceded by the adjacent RPE cell layer dysfunction and death. Exposure of RPE cells to elevated levels of reactive oxygen species (ROS) inhibits the ability of these cells to perform vital functions in the maintenance of retinal health and can lead to cell death. A major external agent responsible for inflicting oxidative damage upon the RPE layer of the human eye is photooxidative damage induced by visible or ultraviolet (UV) light. Therefore, therapeutic strategies aimed at protecting RPE cells against oxidative damage may be particularly important in retarding AMD.

Currently 15 million Americans suffer from signs and symptoms of AMD, and an estimated 27 to 30 million are affected worldwide. Based upon the pattern of progression and pathophysiology, macular degeneration can be divided into two basic types: "dry" and "wet". Approximately 85% to 90% of the cases of AMD are the "dry" (atrophic) type. In the dry form of AMD, areas of focal RPE cell loss develop in the central region termed the macula followed by a loss of the adjacent photoreceptor cells. This phenomena leads to a thinning of the macula, causing loss of function. The resulting blind areas expand at a slow rate but eventually there is significant loss of vision.

SUMMARY

It has been discovered that sulindac can protect photoreceptor and RPE cells in a subject from degenerating in response to photooxidative insults, and that the mechanism of this protection involves peroxisome proliferator-activated receptor alpha (PPAR alpha); protein kinase C (PKC), particularly the epsilon isoform; protein kinase G (PKG); intracellular reactive oxygen species (ROS) generation; and the opening of the mK(ATP) channels of the mitochondria and prevention of the formation of the Mitochondrial permeability transition pore (MTPT).

Described herein are methods of preventing degeneration of photoreceptor cells in an eye of a mammalian subject. This method includes the step of administering an ophthalmically-acceptable pharmaceutical composition comprising a sulindac agent to the eye of the subject. The subject can be one that has been diagnosed with AMD (e.g., dry AMD). The sulindac agent can be sulindac, sulindac sulfone, sulindac sulfide, purified epimers of sulindac, or analogues/derivatives of sulindac. The pharmaceutical composition can be formulated in eye drops and administered topically to the eye. It might also be formulated for injection and administered by intravitreal injection, or as a slow-release device for implantation in the eye. The pharmaceutical composition can include the sulindac agent at between 0.001 to 3% or between 0.005 to 2% by weight. The pharmaceutical composition can have a pH of between 6.5 and 8.0 or between 6.8 and 7.8. The pharmaceutical composition can further include a sterile aqueous buffer and/or dimethylsulfoxide.

As used herein, a "sulindac agent" is sulindac, an epimer of sulindac (e.g., one that has been purified from racemic sulindac), sulindac derivatives, metabolites, analogues, and variants thereof. Examples of sulindac metabolites include sulindac sulfide and sulindac sulfone.

"Ophthalmically-acceptable" refers to the formulation, active agent, excipient or other material compatible with ocular tissue; that is, it does not cause significant or undue detrimental effects when brought into contact with ocular tissue. In some instances, actives and/or excipients of the formulation may cause some discomfort or stinging in the eye; however, those excipients are still considered ophthalmically-acceptable for the purposes of this application.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DESCRIPTION OF THE DRAWING

FIG. 7A is a graph presenting data showing that the protection provided against TBHP by 24 hour preincubation with sulindac is reversed when the cells are treated with the ROS scavenger, tiron (1 uM or 2 uM).

FIG. 7B is a graph presenting data showing that when compared with preincubation with the mK(ATP) channel blocker, 5-HD (50 uM or 75 uM), caused significant reduction in cellular viability in ARPE19 cells exposed to TBHP and sulindac.

DETAILED DESCRIPTION

Figure 1:
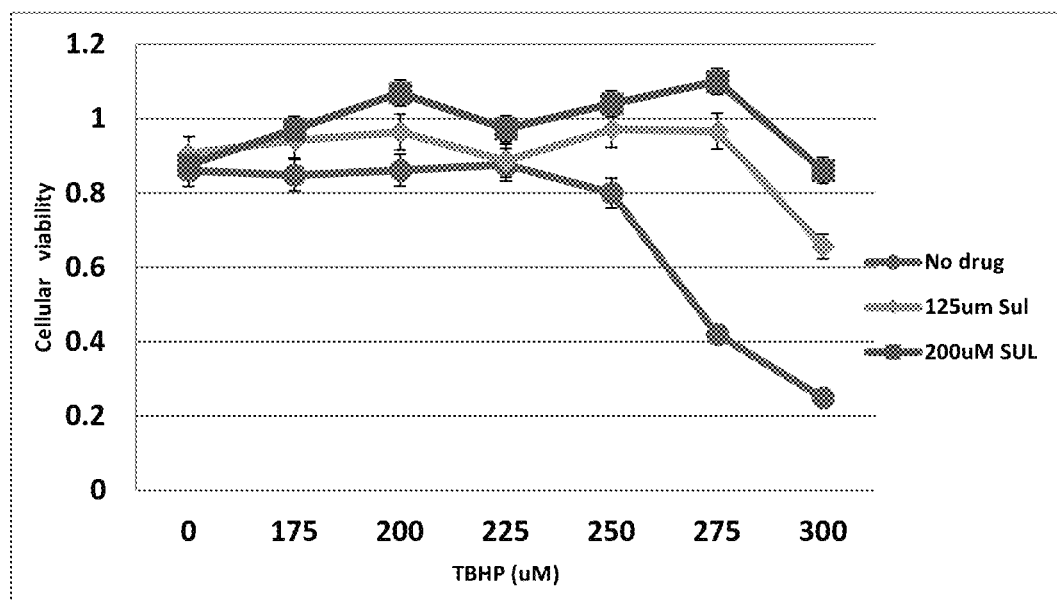
FIG. 1A is a graph presenting data showing that sulindac protects ARPE19 cells from TBHP induced stress in a dose dependent fashion.
FIG. 1B is a graph presenting data showing that sulindac protects ARPE19 cells from UVB induced death.
Figure 1:
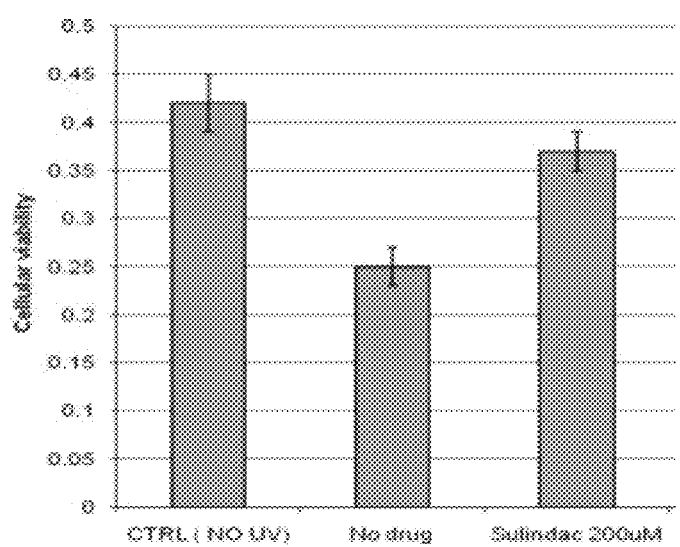

The invention provides methods and compositions for preventing degeneration of photoreceptor cells in an eye of a mammalian subject. The below described embodiments illustrate representative examples of these methods and compositions. Nonetheless, from the description of these embodiments, other aspects of the invention can be made and/or practiced based on the description provided below.

General Methods

Methods involving conventional organic chemistry, medicinal chemistry, pharmaceutical sciences, and drug development techniques are described herein. Such methods are described in: Remington: The Science and Practice of Pharmacy, Lippincott Williams & Wilkins, 21st edition (2005); Drug Discovery and Development, Mukund S. Chorghade (Editor) Wiley-Interscience; 1st edition (2007); The Practice of Medicinal Chemistry, 3rd Edition, Camille Georges Wermuth (Editor) Academic Press; 3rd edition (2008); and Clayden et al., Organic Chemistry, Oxford University Press, 1st edition (2000). Molecular biological and cell biological methods are described in treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

Methods of Preventing Photoreceptor Degeneration

Methods of preventing degeneration of photoreceptor cells in an eye of a mammalian subject can include the step of administering an ophthalmically-acceptable pharmaceutical composition including a sulindac agent to the eye of the subject. The subject can be a mammal such as a human being, a rodent, a cat, a dog, a horse, a sheep, or a pig having or at risk for developing photoreceptor cell degeneration. As non-limiting examples, the subject can be one suffering from, or at risk of developing, AMD (e.g., dry AMD), retinal artery or vein occlusion, diabetic retinopathy, retrolental fibroplasia/retinopathy of prematurity, a paraneoplastic or autoimmune retinopathy, retinitis pigmentosa, or cone-rod dystrophy. The pharmaceutical formulation can be administered to the eye by any suitable method including topically, by injection (e.g., intravitreal or subretinal injection), or implanting a slow-release depot device. For eye drop formulations, administrations can be, without limitation, one to several drops per dose instilled with a frequency of four times per day, thrice per day, twice per day, once a day, or once every 2, 3, 4, 5, 6, 7, 14, or 28 days. For injectable formulations, administrations can be, without limitation, 100 µl to 10 ml, once a day; or once every 2, 3, 4, 5, 6, 7, 14, or 28 days; once every week, 2, 3, 4, 5, or 6 weeks; or once every month, 2, 3, 4, 5, 6, 9, or 12 months. Administration can continue until photoreceptor cell degeneration is retarded (if the underlying condition causing the photoreceptor cell degeneration is corrected) or indefinitely. Photoreceptor cell health can be monitored by methods known in the art, e.g., by electroretinography.

Pharmaceutical Formulations

One or more sulindac agents can be included along with one or more pharmaceutically acceptable carriers or excipients to make pharmaceutical compositions which can be administered to the eye topically or by injection. Suitable formulations for use in the present invention are described in Remington's Pharmaceutical Sciences, Mace Publishing Company, Philadelphia, Pa., 17th ed. (1985). In preferred embodiments, a pharmaceutical composition includes at least 0.001% (e.g., at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0%) sulindac agent by weight. Preferably the composition comprises between 0.001 to 3%, 0.005 to 2%, or 0.005 to 1.5% sulindac agent by weight. For intravitreal injection formulations, the sulindac agent is preferably 0.001 to 0.1% by weight. For topical formulations, the sulindac agent is preferably 0.1 to 3% by weight. The sulindac agent can be, e.g., sulindac, sulindac sulfone, sulindac sulfide, purified epimers of sulindac, or analogues/derivatives of sulindac.

The pharmaceutical composition can be formulated in eye drops (or other formulations such as ointments) for topical administration topically to the eye. Such compositions can have a pH of between 6.5 and 8.5 or between 6.8 and 7.8. Excipients/carriers/other ingredients can include a sterile aqueous buffer, an isotonizing agent, a microbicidal agent or preservative, a chelating agent, a thickening agent, a solubility enhancing agent such as dimethylsulfoxide, and other ingredients. The isotonizing agent can be, e.g., sorbitol, glycerine, polyethylene glycol, propylene glycol, glucose and sodium chloride. The microbicidal agent/preservative can be, e.g., para-oxybenzoic acid esters, benzyl alcohol, para-chloro-meta-xylenol, chlorocresol, phenetyl alcohol, sorbic acid and salts thereof, thimerosal, chlorobutanol, etc. The chelating agent can be, for example, sodium edetate, sodium citrate or sodium salt of condensed phosphoric acid. Ointments can include a base such as petrolatum, macrogol, carboxymethylcellulose sodium, and the like.

The pharmaceutical composition might also be formulated for injection and administered by injection (e.g., intravitreal injection). Such compositions can have a pH of between 6.5 and 8.5 or between 6.8 and 7.8. Excipients/carriers/other ingredients can include a sterile aqueous buffer, an isotonizing agent, a microbicidal agent or preservative, a chelating agent, a solubility enhancing agent such as dimethylsulfoxide, and other ingredients. The isotonizing agent can be, e.g., sorbitol, glycerine, polyethylene glycol, propylene glycol, glucose and sodium chloride. The microbicidal agent/preservative can be, e.g., para-oxybenzoic acid esters, benzyl alcohol, para-chloro-meta-xylenol, chlorocresol, phenetyl alcohol, sorbic acid and salts thereof, thimerosal, chlorobutanol, etc. The chelating agent can be, for example, sodium edetate, sodium citrate or sodium salt of condensed phosphoric acid.

The pharmaceutical composition can also be included in an implantable slow-release depot device that can be placed into an anterior segment or posterior segment of an eye as described in U.S. Pat. No. 4,853,224, e.g. into the suprachoroidal space or pars plana of the eye as described in U.S. Pat. No. 5,164,188, or e.g. into a site extrinsic to the vitreous comprising a suprachoroidal space, an avascular region of an eye, or a surgically-induced avascular region as described in U.S. Pat. No. 5,824,072. In such devices, the sulindac agent can be manufactured into microparticles (e.g., with a particle size of 1 to 200 microns) which are embedded in a biocompatible pharmacologically acceptable polymer or a lipid encapsulating agent.

The depot formulations can be designed to release all or substantially all the active material over an extended period of time, e.g. several weeks up to 6 months. The matrix, e.g. polymer or lipid matrix, if present, is adapted to degrade sufficiently to be transported from the site of administration within one to 6 months after release of all or substantially all the active agent.

Other ingredients that might be included in the above formulations include flocculating and deflocculating agents; an anti-oxidant such as sodium bisulfite, N-acetyl cysteine salts, sodium ascorbate, sodium metabisulfite, or sodium acetone bisulfite; viscosity inducing agents such as hydroxymethyl cellulose, hydroxypropyl cellulose, or methyl cellulose; lecithin; humectants such as high molecular weight sugars; and stabilizing agents such as polyvinylpyrrolidone. The final osmolality of the compositions can be between about 250 to about 350 mOsm.

To enhance half-life, the sulindac agent may be encapsulated, introduced into the lumen of liposomes, prepared as a colloid. A variety of methods are available for preparing liposomes, as described in, e.g., Szoka, et al., U.S. Pat. Nos. 4,235,871, 4,501,728 and 4,837,028 each of which is incorporated herein by reference.

EXAMPLES

Example 1

Methods

Cell culture studies using RPE cells—For cell culture experiments human RPE cell line ARPE19 (ATCC # CRL 2302) purchased from American Type Culture Collection (Rockville, Md.) was used. Cells were maintained in DMEM F-12 supplemented with L-glutamine. The culture media also contained 10% fetal bovine serum, 100 units/ml penicillin and 100 ug/ml streptomycin at 37 C and 5% CO2. Cells from passages two to five were treated with either no drug or a range of concentrations of the experimental drugs prior to exposing them to oxidative stress. Oxidative stress was induced chemically by adding tert-butyl hydrogen peroxide (TBHP) or by exposing the cells to UVB light. ARPE19 cells were plated in 96 well plates at a concentration of 10,000 cells/well. Change in cellular viability was measured using the MTS assay kit from Promega (Madison, Wis.).

Experiments involving TBHP induced oxidative stress—ARPE19 cells were grown for 24 hours in 96 well plates in DMEM F-12 complete media. Then they were either treated with no drug or pre-incubated with the experimental drug for 24 hours. The next day the cells were exposed to a range of concentrations (175 µM to 300 µM) of TBHP for 24 hours. On the following day cell viability was measured by the MTS assay (Promega) according to the manufacturer's protocol and which was measured by absorbance at 490 nm using a colorimetric microtiter plate reader (SpectraMax Plus 384; Molecular Devices).

Exposure of RPE cells to UVB radiation—For UV radiation assays, the ARPE19 cells were plated in 96 well plates. After 24 hours of incubation with or without our drug the cells were exposed to UVB light (Ultraspec 2000, Pharmacia Biotech) that emit wavelengths at a range of 290 nm to 370 nm. UVB light at intensities of either 800 mj/cm2 or 1200 mj/cm2 were used for our experiments. The duration of exposure of the two energy levels were determined using the formula: $H\lambda = t \times E\lambda$, where $H\lambda$ is the energy level (J/cm2) t is the duration of exposure in seconds and the $E\lambda$ is the irradiance (W/cm2) of the UVB source. Irradiance was measured at 1.3 W/cm2, and the exposure times for energy levels of 800 mj/cm2 and 1200 mj/cm2 were calculated to be 9 minutes 14 seconds and 14 minutes 24 seconds, respectively. Immediately after the UVB exposure, the media was replaced with fresh complete DMEM F-12 medium and after 24 hours of incubation at 37° C. and 5% CO2, cellular viability was measured using the MTS assay.

Blocking of PKC pathways—To investigate the involvement of the PKC pathway in the preconditioning mechanism, the PKC inhibitor chelerythrine (Sigma) was used at a concentration of 2 uM. The inhibitor was added simultaneously with the drug prior to exposing the cultured cells to oxidative stress. To further analyze which specific isoform of PKC is involved in the protective mechanism offered by sulindac, two separate inhibitors for the two PKC isoforms, PKCε and PKCδ, were tested. For PKCε the inhibitor used was the peptide V1-V2 (10 uM) and for the inhibition of the PKC's δ isoform rottlerin (Sigma) was used (3 uM). The inhibitors were added at the same time as the drug prior to exposing the cells to TBHP. The PKCε isoform blocker, V1-V2 peptide, was added at a final concentration of 10 uM and rottlerin was used at a concentration of 3 uM.

Cell viability assays—Cellular viability was determined using the CellTiter 96 Aqueous One Cell Proliferation Assay from Promega (Madison, Wis.) as described elsewhere (Marchetti et al, 2009). This assay contains a tertrazolium salt that is converted to formazan dye by the activity of mitochondrial dehydrogenases. The change in color imparted by this conversion was detected by measuring absorbance at 490 nm using a colorimetric microtiter plate reader (Spectramax Plus 384, Molecular Devices).

Western blotting protocol—Western blotting was carried out on proteins isolated from ARPE19 cells cultured in 60 mm dishes with no drug or 200 μM sulindac or a combination of 200 μM sulindac and 2 μM chelerythrine. Actin and GAPDH were used as control for standardizing protein concentrations. Two late phase preconditioning markers, Hsp27 and iNOS were detected with antibodies (Sant Cruz Biotechnology).

Photooxidative stress in vivo study—The procedures for the in vivo experiments conformed to the ARVO Statement for the Use of Animals in Ophthalmic and Vision Research and were approved by the IACUC at FAU. For the in vivo photooxidative stress experiments albino BALB/c mice were divided into two groups. Mice belonging to the control group were kept in normal light of 12 hr light/dark cycle and not injected with any drug. The animals of the experimental group were dark-adapted for 24 hours after which they were anesthetized with ketamine/xylazine and injected intravitrealy with sulindac, total volume injected was 2 μl in each eye. Concentration of injected sulindac was 0.094 μg/μl. To prepare our injection, the sulindac powder was first dissolved in Tris buffer (pH 8.0) at a concentration of 200 mM. This 200 mM stock was further diluted in sterile PBS to get the appropriate dilution required for the injections. The sulindac solution was injected into the right eye and PBS in the left eye. The animals in the experimental group received atropine for pupil dilation followed by exposure to continuous bright white light. The intensity and duration of light exposure was 6000 lux for 24 hours. Following light exposure, animals were kept in normal light cycle for 5 days prior to harvesting the ocular tissues for histological or biochemical analysis.

Biochemical analysis of ocular tissues—After the completion of the treatment, animals were euthanized using isoflurane inhalation and eyes were enucleated. Following enucleation, the lenses were removed and retinas were carefully removed and washed in PBS. The retinas were homogenized in RIPA lysis buffer and total protein was isolated. The retinal protein was used for evaluation of preconditioning markers and rhodopsin through Western blotting.

Analysis of photoreceptor (PR) cell viability—The eyes were enucleated and fixed in 2.5% glutaraldehyde and 2% formaldehyde, bisected along the vertical meridian, embedded, and retinal sections at 50 microns obtained. Photoxidative stress-induced loss of PR cells was quantified in LM sections by counting the number of ONL nucei from a series of digitized images of retinal sections.

Statistical analysis—Unless otherwise mentioned, results of all cell viability experiments represent the mean of three replicates of a representative experiment. The error bars indicate standard deviations. The means were compared using standard t-test and P values <0.05 were considered to be statistically significant.

Example 2

Results—Protection of Retinal Cells by Sulindac

Sulindac protects ARPE19 cells from chemical oxidative stress and UV induced photooxidative stress: As described in Methods two types of oxidative stress were used in these experiments, either exposure of the RPE cells to an oxidizing agent such as TBHP, or exposure to UV light. In these experiments the RPE cells were pretreated for 24 hours with varying concentrations of sulindac, sulindac sulfone as shown in the FIG. 1. FIG. 1A shows the effect of sulindac in protecting RPE cells against varying concentrations of TBHP as measured by cell viability, whereas FIG. 1B shows the protection of the RPE cells against UV damage by sulindac, using 1200 mjoules of UV radiation. As seen in FIG. 1A, sulindac at concentrations of 125 and 200 uM afforded essentially complete protection against TBHP damage. FIG. 1B shows that sulindac, at 200 uM can provide about 50% protection against 1200 mj of UVB exposure.

Figure 2:
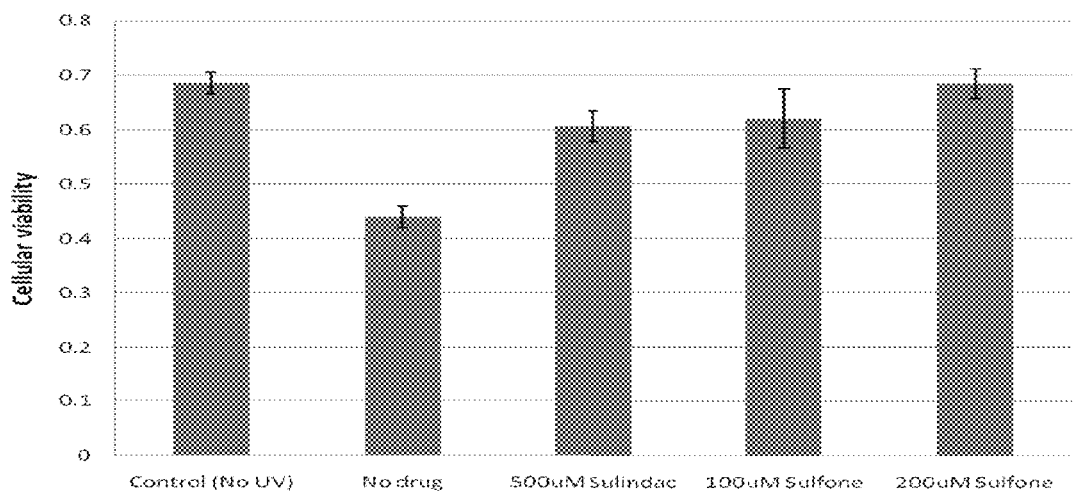
FIG. 2 is a graph presenting data showing that the oxidized sulfone form of sulindac, which lacks NSAID activity, also protects RPE cells against UVB damage.

Protection by sulindac is not based on COX inhibition—To determine whether this protective effect was due to the NSAID activity of sulindac, sulindac sulfone, a metabolite of sulindac that has no NSAID activity was tested in place of sulindac for its UV protective effect. As shown in FIG. 2, sulindac sulfone at 200 uM concentration provides complete protection against UV damage. It should also be noted that sulindac sulfone is not a substrate for the Msr system which eliminates the possibility that the sulindac protective effect was related to its being a substrate for the Msr enzymes and functioning as a catalytic anti-oxidant in an ROS scavenging system (Stadtman et al.).

Figure 3A:
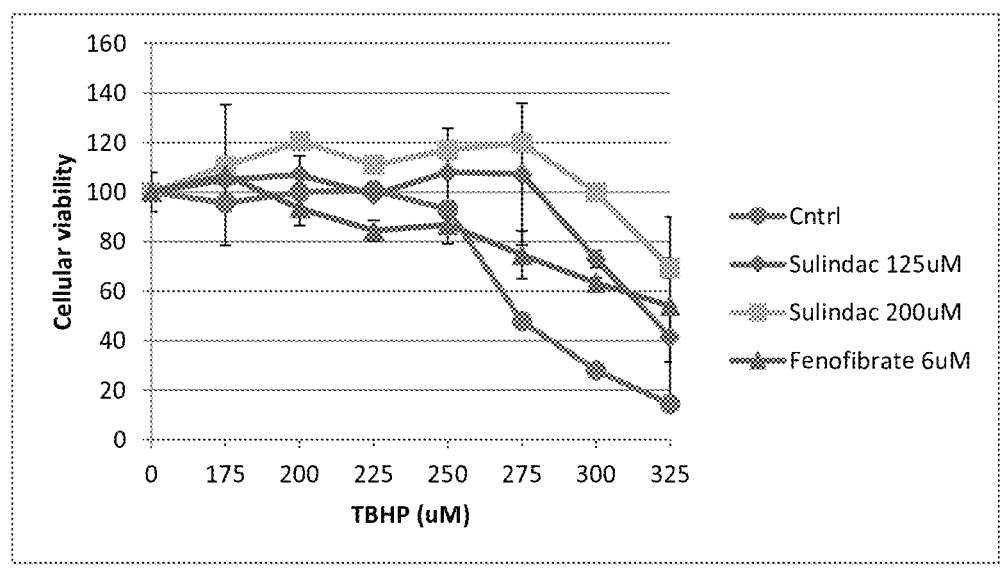
FIG. 3A is a graph presenting data showing that the protective mechanism of sulindac can be replaced with a PPAR alpha antagonist where Fenofibrate protects ARPE19 cells against TBHP.
Figure 3B:
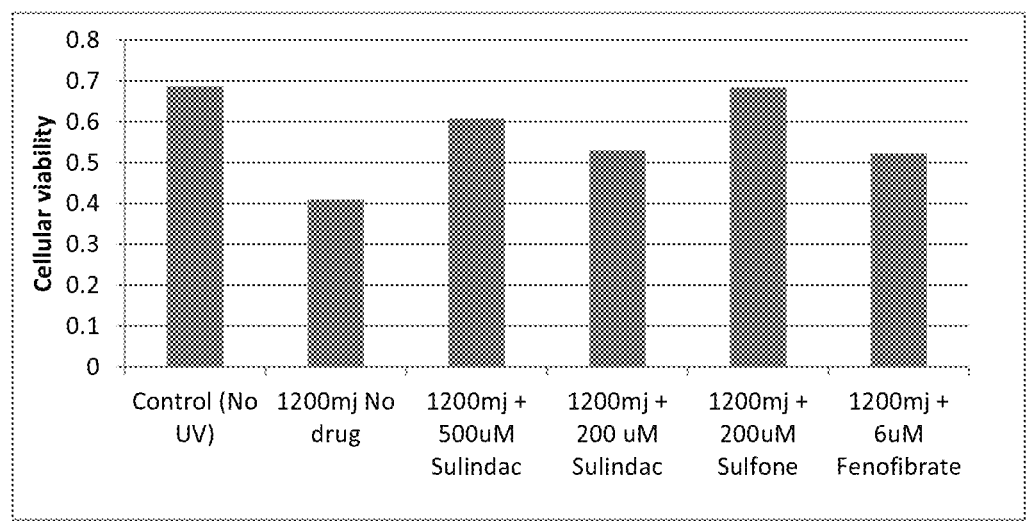
FIG. 3B is a graph presenting data showing that the protective mechanism of sulindac can be replaced on a PPAR alpha antagonist as shown in FIG. 3B, where Fenofibrate protects ARPE19 cells against UVB.
Figure 3C:
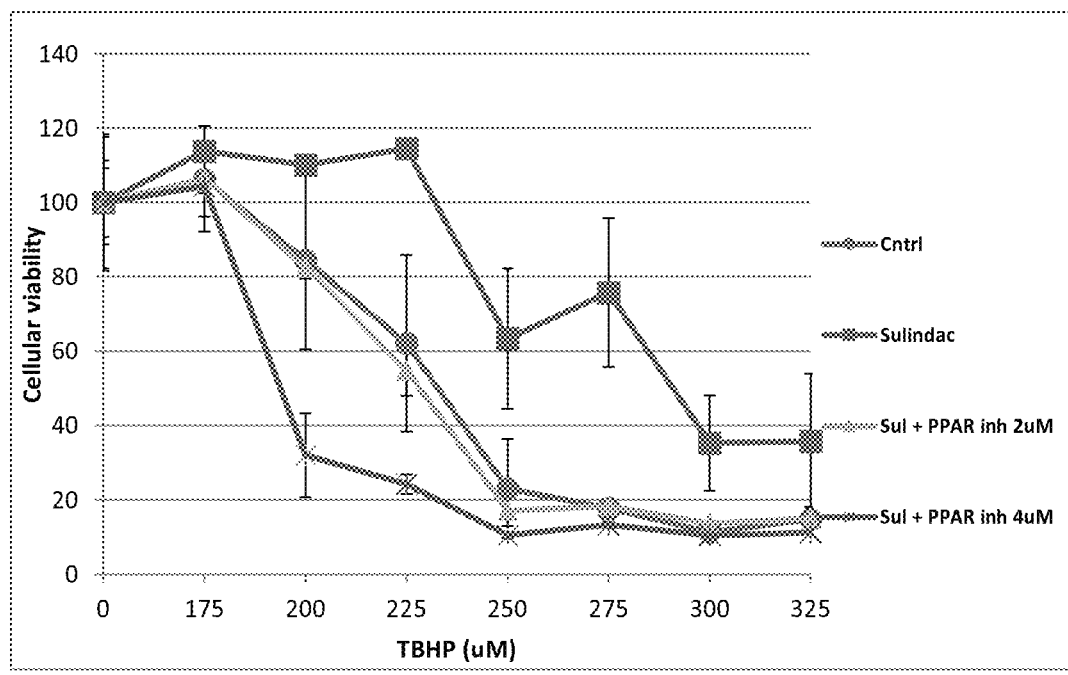
FIG. 3C is a graph presenting data showing that the protection by sulindac is reversed by a PPAR antagonist.

Activation of PPAR alpha is involved in the protective mechanism of sulindac—When sulindac was substituted with the PPAR agonist, fenofibrate (6 uM) it offered protection to cultured ARPE19 cells against oxidative stress induced by both methods, TBHP (FIG. 3A) or UVB light (FIG. 3B) and the efficacy of protection was found to be comparable to that offered by sulindac. To provide further evidence of involvement of PPAR alpha, the effect of a chemical inhibitor of PPAR alpha on sulindac's protective ability against oxidative stress was examined. For these experiments GW 6471, a PPAR alpha antagonist, was used which prevented the protection of RPE cells against TBHP induced stress by sulindac (FIG. 3C) supporting the involvement of PPAR in the sulindac mechanism.

Figure 4A:
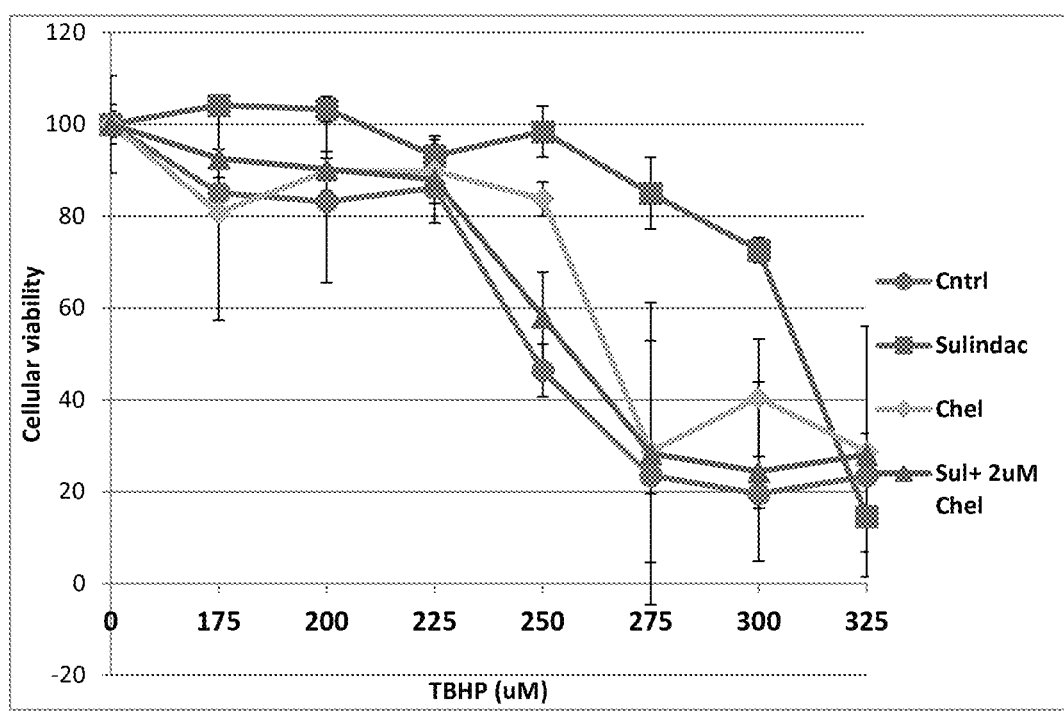
FIG. 4A is a graph presenting data showing that Chelerythrine an inhibitor of PKC isoforms reverses (or prevents) protection against oxidative stress by sulindac against TBHP damage.
Figure 4B:
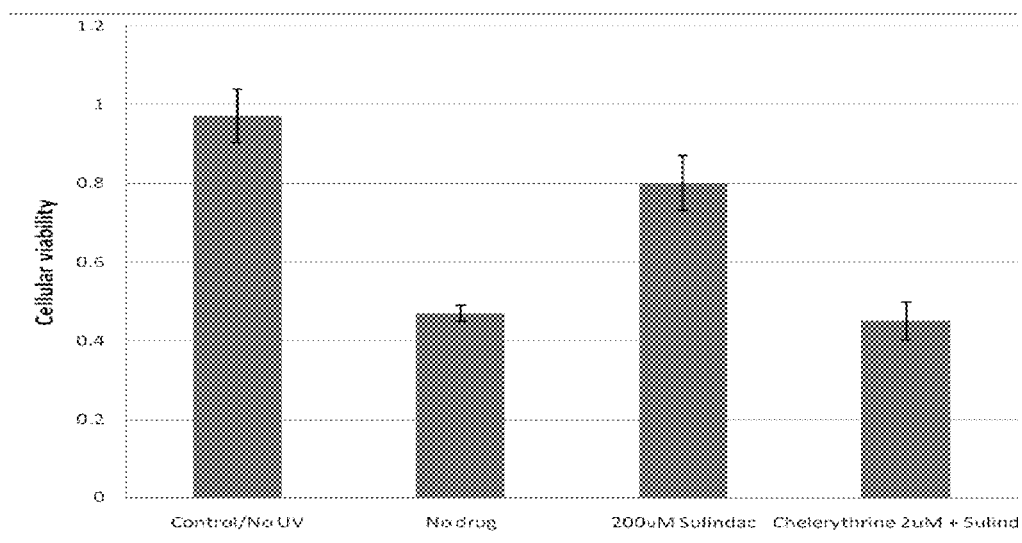
FIG. 4B is a graph presenting data showing that Chelerythrine an inhibitor of PKC isoforms reverses (or prevents) protection against oxidative stress by sulindac against UVB light damage.

Protection by sulindac is dependent on PKC—To understand the mechanism of protection the possible role of PKC in the protection of RPE cells by sulindac was examined. As shown in FIGS. 4A and 4B, chelerythrine, a broad spectrum PKC inhibitor, significantly reversed the protective effect of sulindac on cultured RPE cells against TBHP and UV damage, suggesting that one or more isoforms of PKC were involved in the sulindac protective effect.

Figure 5A:
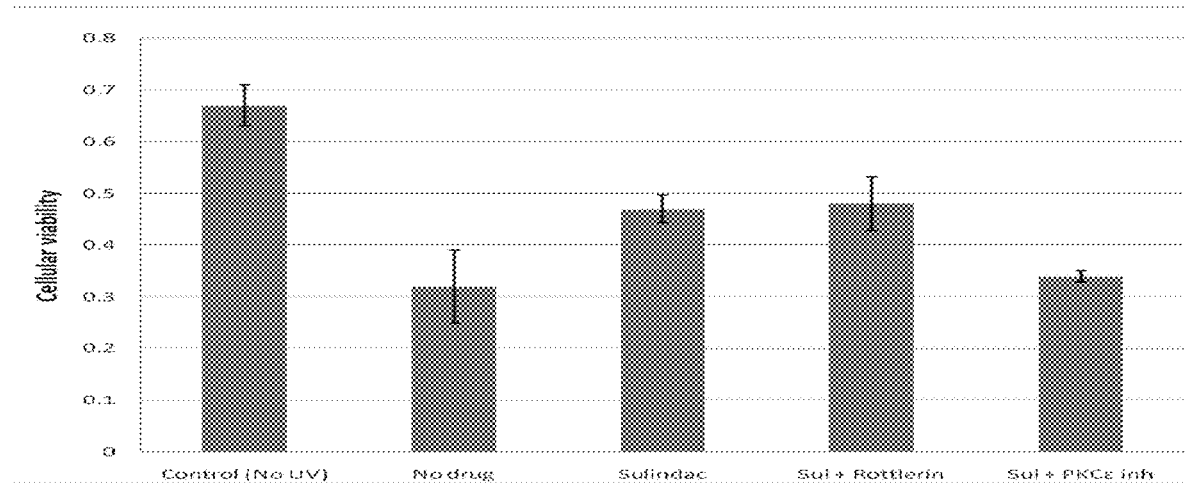
FIG. 5A is a graph presenting data showing that incubation with the PKC epsilon specific inhibitor peptide V1-V2 (10 uM) significantly reduces sulindac's protective efficacy in the UVB assay, but PKC delta inhibition by rottlerin (3 uM) did not inhibit protection by sulindac.
Figure 5B:
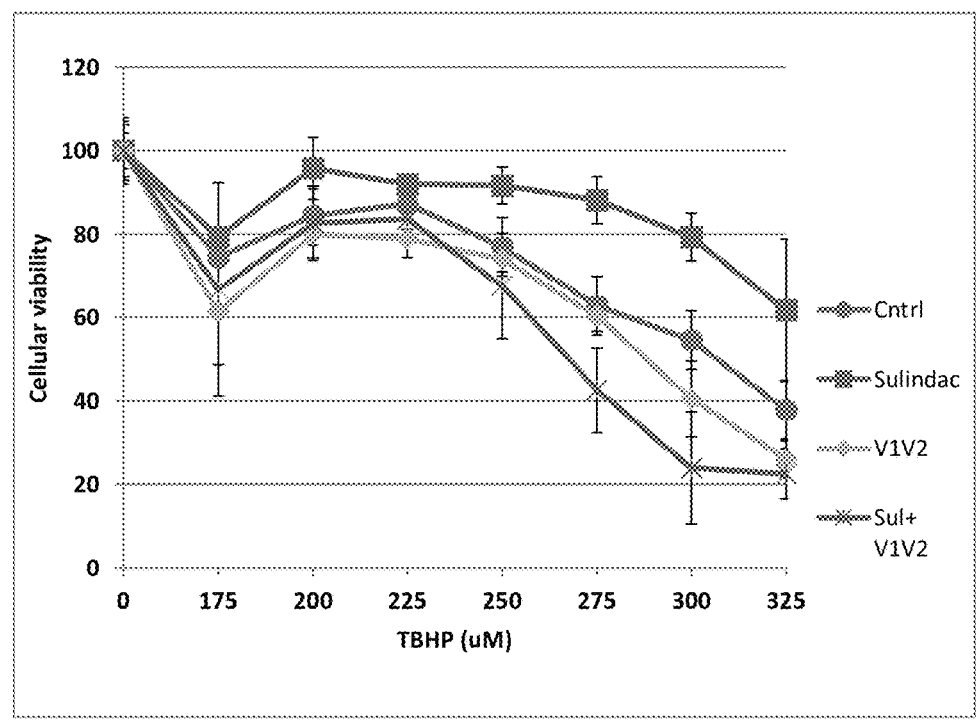
FIG. 5B is a graph presenting data showing that coincubation of sulindac with V1-V2 reverses its protective ability against TBHP induced stress.
Figure 6:
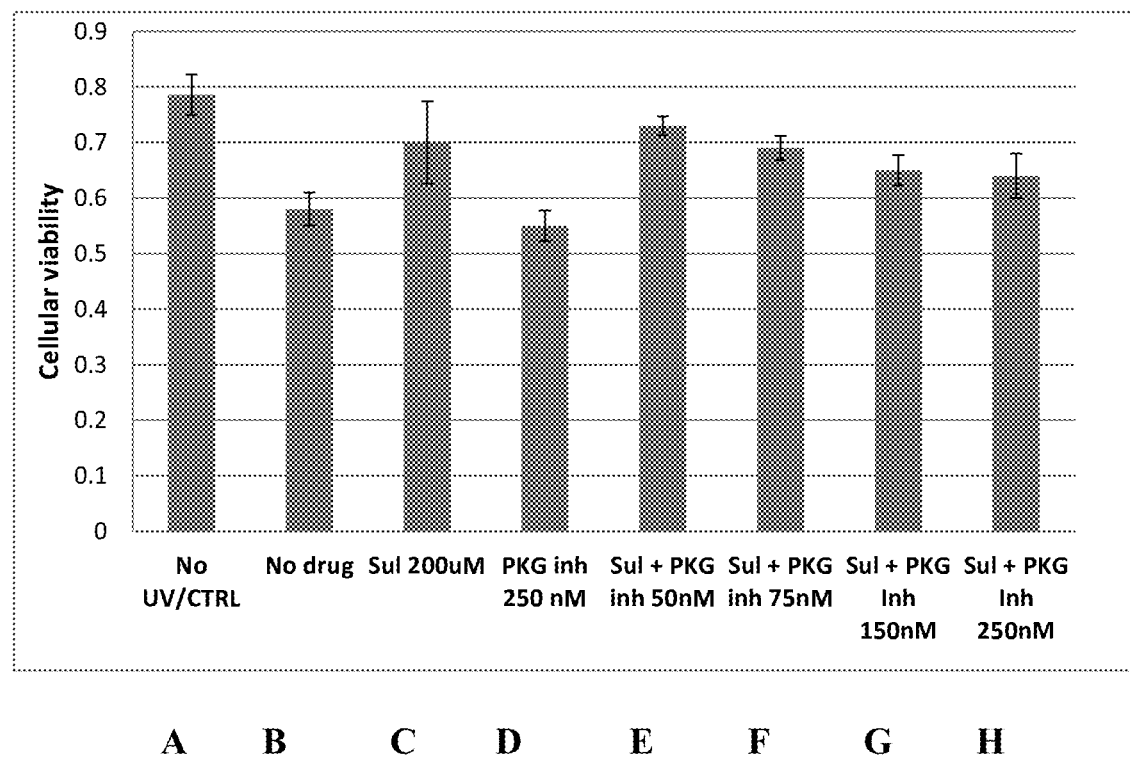
FIG. 6 is a graph presenting data showing that PKG is involved in the preconditioning mechanism Inhibition of PKG using PKG the chemical inhibitor Rp-8-Bromo-PET-cGMPS, prevents the UVB damage protective effect by sulindac.

Involvement of PKC epsilon but not PKC delta—As shown in FIG. 5A, V1-V2, a peptide inhibitor of PKC epsilon almost completely reversed the protective effect of sulindac against UVB. In contrast, rottlerin, a PKC delta inhibitor, when used at 3 uM, a concentration reported to inhibit PKC delta, showed no reversal of the sulindac protection. FIG. 5B shows that V1-V2 also reverses the sulindac protective effect against TBHP Protection by sulindac is dependent on PKG: The reversal of protection produced by preincubation with sulindac was significantly reversed when PKG was inhibited by, Rp-Br-8-PET-cGMPs (FIG. 6).

Figure 7A:
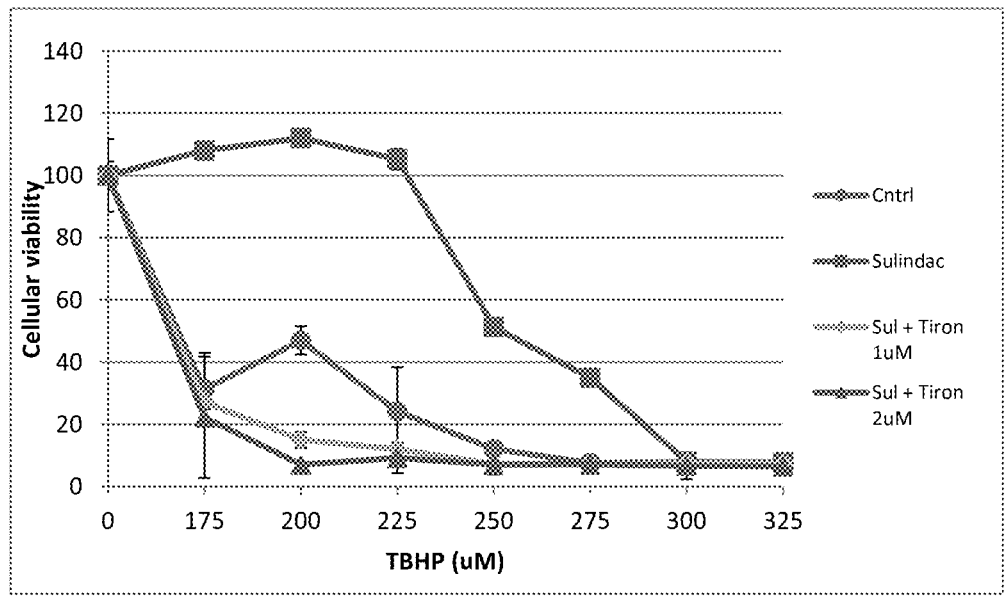
FIGS. 7A and 7B are two graphs showing that preconditioning by sulindac involves intracellular ROS generation and opening of the mK(ATP) channels of the mitochondria.
Figure 7B:
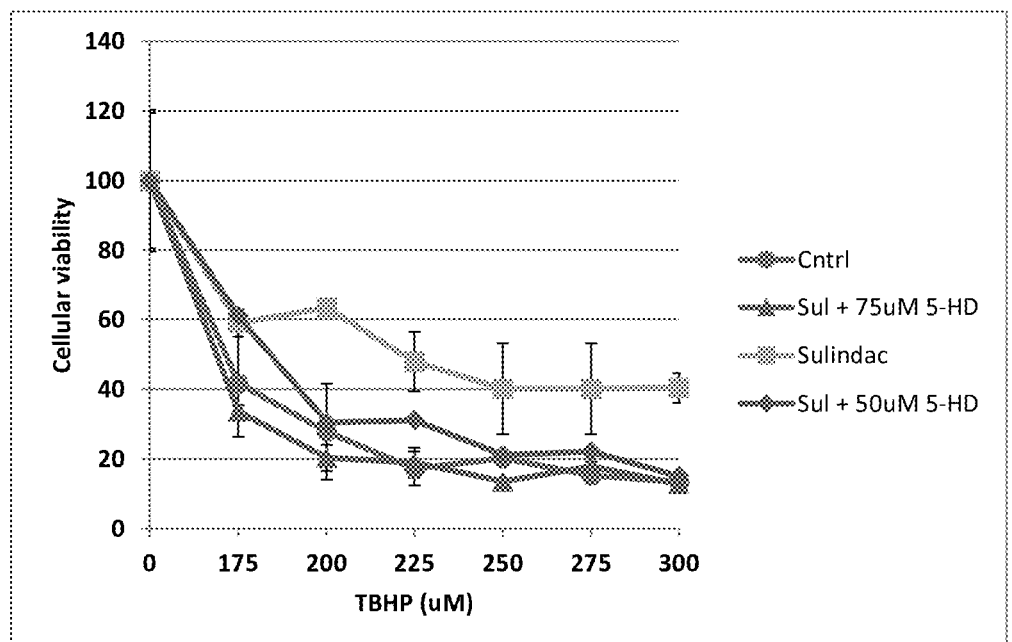

ROS generation by sulindac in involved in the protection of RPE cells against oxidative stress. In order to confirm the role of ROS in the sulindac protection, cultured ARPE19 cells were coincubated with the ROS scavenger tiron along with sulindac, prior to exposure to TBHP. The presence of tiron caused complete reversal of sulindac's protection (FIG. 7A) providing further evidence in favor of involvement of increased ROS levels in this protective mechanism. The possible role of mitochondrial K/ATP (ATP sensitive K+ channel) was also analyzed. As shown in FIG. 7B, co-incubation of the cells with sulindac and 5-hydroxydecanoic acid (5-HD), a chemical inhibitor of the mitochondrial K/ATP channel, caused almost complete reversal of sulindac's protective role, indicating the involvement of the mitochondrial membrane channels.

Figure 8:
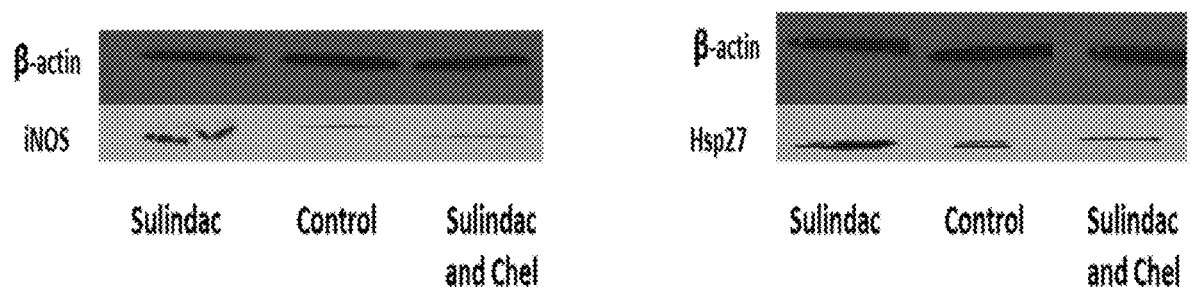
FIG. 8 is a Western blot analysis showing that sulindac preincubation causes induction of the preconditioning markers iNOS and Hsp 27, where indicated. Chelerythrine 2 uM, an inhibitor of PKC was added.

Precondition markers are upregulated in cells incubated with sulindac—As shown in FIG. 8, there was significant induction of iNOS and Hsp27 in RPE cells pretreated for 48 hours with sulindac.

Figure 9A:
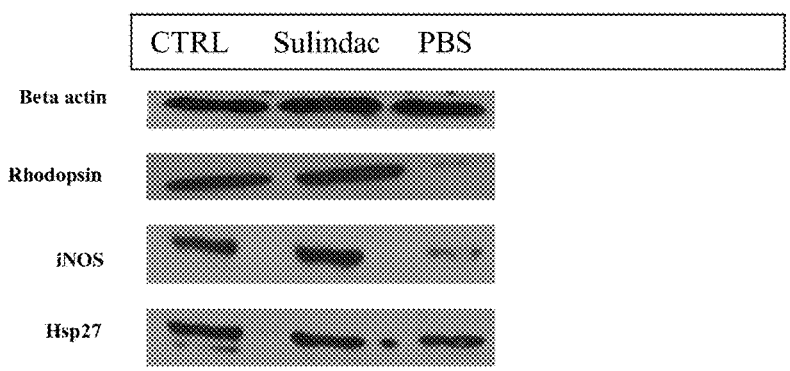
FIG. 9A is a Western blot showing that sulindac upregulates preconditioning markers in vivo and provides protection against photooxidative stress in BALB/c mice.
Figure 9B:
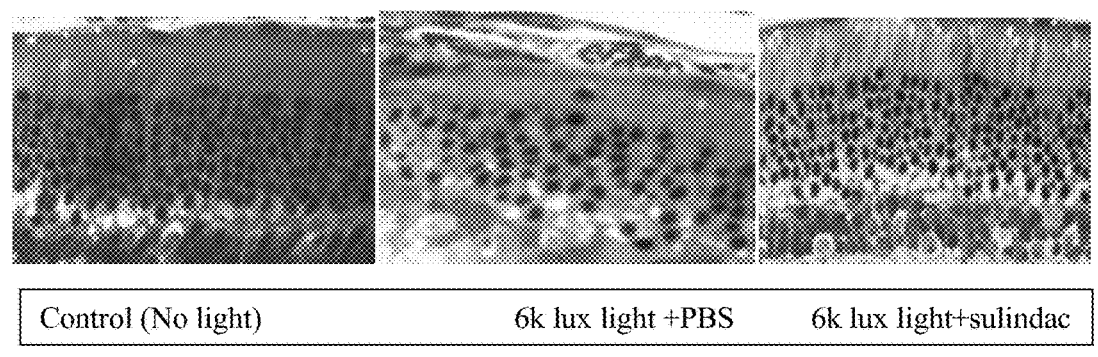
FIG. 9B is a series of photomicrographs showing that sulindac upregulates preconditioning markers in vivo and provides protection against photooxidative stress in BALB/c mice.

In vivo experiments in mice showed that retinal cells are protected by sulindac against light induced damage. In order to establish the therapeutic efficacy and clinical significance of sulindac as a protective agent for retinal cells against oxidative stress, a light damage BALB/c mouse study in which sulindac was injected intravitrealy prior to light exposure was used. Photooxidative stress was induced by exposing BALB/c mice to bright white light of 6000 lux for a period of 24 hours. Comparative histological analysis of the retina from control and experimental animals revealed that pretreatment with sulindac prior to exposure to our light damage paradigm resulted in protection of photoreceptors against photooxidative stress induced loss of viability. Rhodopsin levels as measured by Western blotting (FIG. 9A) and the thickness of the photoreceptor cell nuclear layer in histological sections (FIG. 9B) were both higher in the sulindac-treated eye compared to the PBS-treated eye. In the latter figure, the thickness of the photoreceptor cell nuclear layer in the sulindac-treated eye was about 40% greater than the PBS-treated eye. To determine the possible involvement of IPC in the in vivo protection, changes in the levels of the same two markers of preconditioning, Hsp27 and iNOS, were evaluated in RPE cell culture studies. As shown in FIG. 9A, Western blotting of retinal total protein showed upregulation of both of the late preconditioning markers in the eyes treated with sulindac prior to light exposure, indicating that IPC mechanism is associated with the protection of PR cells in this in vivo study.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating oxidative stress-induced degeneration of photoreceptor cells and retinal pigment epithelial cells in an eye of a mammalian subject with dry macular degeneration, the method comprising the step of administering an ophthalmically-acceptable pharmaceutical composition comprising a sulindac agent to the eye of the subject in an amount sufficient to reduce oxidative stress-induced degeneration of photoreceptor cells and retinal pigment epithelial cells in the eye of a mammalian subject, wherein the oxidative stress-induced degeneration of photoreceptor cells and retinal pigment epithelial cells in the eye of a mammalian subject is reduced after the step of administering the pharmaceutical composition.

2. The method of claim 1, wherein the sulindac agent is sulindac.

3. The method of claim 1, wherein the sulindac agent is sulindac sulfone.

4. The method of claim 1, wherein the sulindac agent is sulindac sulfide.

5. The method of claim 1, wherein the pharmaceutical composition is formulated in eye drops and administered topically to the eye.

6. The method of claim 1, wherein the pharmaceutical composition is formulated for injection and administered by intravitreal injection.

7. The method of claim 1, wherein the pharmaceutical composition comprises the sulindac agent at between 0.001 to 3% by weight.

8. The method of claim 1, wherein the pharmaceutical composition comprises the sulindac agent at between 0.005 to 2% by weight.

9. The method of claim 1, wherein the pharmaceutical composition has a pH of between 6.5 and 8.0.

10. The method of claim 1, wherein the pharmaceutical composition has a pH of between 6.8 and 7.8.

11. The method of claim 1, wherein the pharmaceutical composition comprises a sterile aqueous buffer and dimethylsulfoxide.

* * * * *